US012421497B2

(12) United States Patent
Yoshida et al.

(10) Patent No.: US 12,421,497 B2
(45) Date of Patent: Sep. 23, 2025

(54) METHOD FOR ENRICHING CARDIAC MYOCYTES

(71) Applicant: Orizuru Therapeutics, Inc., Fujisawa (JP)

(72) Inventors: Yoshinori Yoshida, Kyoto (JP); Kenji Miki, Kyoto (JP); Misato Koakutsu, Kyoto (JP)

(73) Assignee: Orizuru Therapeutics, Inc., Kanagawa (JP)

( * ) Notice: Subject to any disclaimer, the term of this patent is extended or adjusted under 35 U.S.C. 154(b) by 846 days.

(21) Appl. No.: 17/636,561

(22) PCT Filed: Aug. 19, 2020

(86) PCT No.: PCT/JP2020/031194
§ 371 (c)(1),
(2) Date: Feb. 18, 2022

(87) PCT Pub. No.: WO2021/033699
PCT Pub. Date: Feb. 25, 2021

(65) Prior Publication Data
US 2022/0298482 A1    Sep. 22, 2022

(30) Foreign Application Priority Data

Aug. 20, 2019  (JP) ................. 2019-150593
Mar. 30, 2020  (JP) ................. 2020-059409

(51) Int. Cl.
*C12N 5/077*   (2010.01)

(52) U.S. Cl.
CPC ........ *C12N 5/0657* (2013.01); *C12N 2500/24* (2013.01); *C12N 2500/32* (2013.01); *C12N 2501/115* (2013.01); *C12N 2501/155* (2013.01); *C12N 2501/16* (2013.01); *C12N 2501/165* (2013.01); *C12N 2506/45* (2013.01)

(58) Field of Classification Search
CPC .............. C12N 5/0657; C12N 2500/24; C12N 2500/32; C12N 2501/115; C12N 2501/155; C12N 2501/16; C12N 2501/165; C12N 2506/45
See application file for complete search history.

(56) References Cited

U.S. PATENT DOCUMENTS

| 2007/0202590 A1 | 8/2007 | Shinohara et al. |
| 2011/0086379 A1 | 4/2011 | Blak et al. |
| 2013/0209416 A1 | 8/2013 | Ma |
| 2015/0299658 A1 | 10/2015 | Ma |
| 2016/0083715 A1 | 3/2016 | Rasmusson et al. |
| 2017/0207576 A1* | 7/2017 | Noack et al. |
| 2019/0062696 A1 | 2/2019 | Chien et al. |
| 2021/0054406 A1 | 2/2021 | Yoshida et al. |

FOREIGN PATENT DOCUMENTS

| CA | 2684878 A1 | 7/2008 |
| CN | 2374871 A1 * | 10/2011 |
| CN | 102605057 A | 7/2012 |
| CN | 102762718 A | 10/2012 |
| CN | 107460164 A | 12/2017 |
| CN | 108410802 A | 8/2018 |
| EP | 2 374 871 A1 | 10/2011 |
| JP | 2013-531497 * | 8/2013 |
| JP | 2013-531497 A | 8/2013 |
| JP | 2015-527886 * | 9/2015 |
| JP | 2015-527886 A | 9/2015 |
| JP | 2016-518853 A | 6/2016 |
| WO | WO-2005/100548 A1 | 10/2005 |
| WO | WO-2017/207576 A1 | 12/2017 |
| WO | WO-2019/189545 A1 | 10/2019 |

OTHER PUBLICATIONS

Chien, et al. "Regulation of CD151 by hypoxia controls cell adhesion and metastasis in colorectal cancer." Clinical Cancer Research; 14(24) Dec. 15, 2008. (Year: 2008).*
Office Action and Search Report dated Dec. 29, 2023 in CN 202080057254.0, with English translation.
Wei et al., "Adeno-associated Viral Vector Mediated and Cardiac-specific Delivery of CD151 Gene in Ischemic Rat Hearts," Journal of Huazhong University of Science and Technology (Med. Sci.), Feb. 19, 2011, 31(1):46-51.
International Search Report dated Sep. 29, 2020 in PCT/JP2020/031194.
Lee et al., "Human Pluripotent Stem Cell-Derived Atrial and Ventricular Cardiomyocytes Develop from Distinct Mesoderm Populations," Cell Stem Cell, Aug. 3, 2017, 21(2):179-194.
Wiencierz et al., "Differential Expression Levels of Integrin a6 Enable the Selective Identification and Isolation of Atrial and Ventricular Cardiomyocytes," Plos One, Nov. 30, 2015, 10(11):e0143838, 1-20.
Koakutsu et al., "Abstract 13726: Identification of a Cell Surface Marker Which is Differentially Expressed Between Ventricular and Atrial Cardiomyocytes Derived From Human Induced-Pluripotent Stem Cell," Circulation, Nov. 11, 2019, 140:A13726, 1-6.
Supplementary European Search Report dated Jul. 14, 2023 in EP 20853941.1.

* cited by examiner

*Primary Examiner* — Allison M Fox
*Assistant Examiner* — Gina Pronzati
(74) *Attorney, Agent, or Firm* — Foley & Lardner LLP

(57) ABSTRACT

As a technology for enriching atrial myocytes or ventricular myocytes in a cardiomyocyte-containing cell population induced from stem cells, provided is a method for enriching atrial myocytes or ventricular myocytes in a cardiomyocyte-containing cell population induced from stem cells, the method including a step of collecting atrial myocytes or ventricular myocytes from the cell population by using the expression level of CD151 as an index.

4 Claims, 5 Drawing Sheets

(A) Action potential waveform before or after 4-aminopyridine addition (B) Action potential waveform before or after carbachol addition

METHOD FOR ENRICHING CARDIAC MYOCYTES

CROSS-REFERENCE TO RELATED APPLICATIONS

This application is the U.S. National Stage of PCT/JP2020/031194, filed Aug. 19, 2020, which claims priority to JP 2019-150593, filed Aug. 20, 2019 and JP 2020-059409, filed Mar. 30, 2020.

TECHNICAL FIELD

The present invention relates to a method for enriching atrial myocytes or ventricular myocytes in a cardiomyocyte-containing cell population induced from stem cells and the like.

BACKGROUND ART

Cardiomyocytes have been induced from stem cells such as induced pluripotent stem cells (iPSCs) or embryonic stem cells (ESCs) to be used for regenerative medicine for cardiac diseases.

The functions of atrial myocytes differ from those of ventricular myocytes. A cardiomyocyte-containing cell population induced from stem cells should contain multiple types of cardiomyocytes including atrial myocytes and ventricular myocytes, and may further contain non-cardiomyocytes such as undifferentiated cells. In view of this, for applying a cardiomyocyte-containing cell population may be induced from stem cells to regenerative medicine, it is desirable to enrich, depending on the treatment purpose, either atrial myocytes or ventricular myocytes in the cell population.

Non-Patent Literature 1 discloses a technology for separating atrial myocytes and ventricular myocytes from cardiomyocytes isolated from a mouse fetal or neonatal tissue by using Integrin 6 as a marker.

In addition, Non-Patent Literature 2 discloses a technology for separating cardiomyocytes induced from iPSCs into atrial myocytes and ventricular myocytes by using CD235a and RALDH2 as markers.

CITATION LIST

Non Patent Literature

Non Patent Literature 1: "Differential Expression Levels of Integrin α6 Enable the Selective Identification and Isolation of Atrial and Ventricular Cardiomyocytes", PLoS One, 2015, 10(11): e0143538.

Non Patent Literature 2: "Human Pluripotent Stem Cell-Derived Atrial and Ventricular Cardiomyocytes Develop from Distinct Mesoderm Populations", Cell Stem Cell, 2017, 21(2): 179-194.

SUMMARY OF INVENTION

Technical Problem

The main object of the present invention is to provide technology for enriching atrial myocytes or ventricular myocytes in a cardiomyocyte-containing cell population induced from stem cells.

Solution to Problem

To solve the above problem, the present invention provides the following [1] to [20].

[1] A method for enriching atrial myocytes or ventricular myocytes in a cardiomyocyte-containing cell population induced from stem cells, comprising a step of collecting atrial myocytes or ventricular myocytes from the cell population by using an expression level of CD151 as an index.

[2] The method according to [1], comprising a step of collecting CD151 low expressing cells from the cell population, thereby enriching the atrial myocytes.

[3] The method according to [1], comprising a step of collecting CD151 high expressing cells from the cell population, thereby enriching the ventricular myocytes.

[4] The method according to any one of [1] to [3], wherein the stem cells are induced pluripotent stem cells.

[5] A cell population obtained by the method according to [1], wherein atrial myocytes or ventricular myocytes are enriched.

[6] A cell population obtained by the method according to [2], wherein atrial myocytes are enriched.

[7] A cell population obtained by the method according to [3], wherein ventricular myocytes are enriched.

[8] A pharmaceutical comprising the cell population according to any one of [5] to [7].

[9] A process for producing atrial myocytes or ventricular myocytes from stem cells, comprising the steps of:
(A) inducing a cardiomyocyte-containing cell population from the stem cells; and
(B) collecting atrial myocytes or ventricular myocytes from the cell population by using an expression level of CD151 as an index.

[10] The process according to [9], comprising steps of:
(A) inducing a cardiomyocyte-containing cell population from the stem cells under conditions for differentiation into atrial myocytes; and
(B) collecting CD151 low expressing cells from the cell population, thereby producing the atrial myocytes.

[11] The process according to [9], comprising steps of:
(A) inducing a cardiomyocyte-containing cell population from the stem cells under conditions for differentiation into ventricular myocytes; and
(B) collecting CD151 high expressing cells from the cell population, so thereby producing the ventricular myocytes.

[12] The process according to any one of [9] to [11], wherein the stem cells are induced pluripotent stem cells.

[13] An atrial myocyte or ventricular myocyte obtained by the production process according to [9].

[14] An atrial myocyte obtained by the production process according to [10].

[15] A ventricular myocyte obtained by the production process according to [11].

[16] A pharmaceutical comprising atrial myocytes or ventricular myocytes obtained by the production process according to any one of [9] to [11].

[17] A reagent for enriching atrial myocytes or ventricular myocytes in a cardiomyocyte-containing cell population induced from stem cells, comprising a CD151 detection probe.

[18] The reagent according to [17], wherein the CD151 detection probe is an anti-CD151 antibody.

[19] Use of a CD151 detection probe for enriching atrial myocytes or ventricular myocytes in a cardiomyocyte-containing cell population induced from stem cells.

[20] Use of CD151 as a marker for enriching atrial myocytes or ventricular myocytes in a cardiomyocyte-containing cell population induced from stem cells.

[Definitions]

As used herein, the term "cell population" means an assembly containing two or more different types of cells. The "cell subpopulation" refers to a homogeneous or heterogeneous cell assembly constituting a cell population, and means a group of cells which share at least one characteristic.

The term "enrich" or "enrichment" refers to increasing the amount of specific component in a composition such as a cell composition. The term "enriched" refers to, in the case of describing a cell composition such as a cell population, an increase in the amount of specific component when compared to the percentage of the component in the pre-enriched cell population. For example, a composition such as a cell population may contain enriched target cell types, and thus the percentage of the target cell type is larger than the percentage of the target cell present in the pre-enriched cell population. The cell population can contain a target cell type(s) enriched by a cell selection or sorting procedure known in the art. The cell population may be enriched by a specific selection or sorting process described herein. In a certain embodiment of the invention, the target cell population in the post-enriched cell population is enriched, compared with the pre-enriched cell population, by at least 1%, 2%, 3%, 4%, 5%, 6%, 7%, 8%, 9%, 10%, 20%, 30%, 40%, 50%, 60%, 70%, 80%, 85%, 90%, 95%, 97%, 98%, or 99%. In another certain embodiment of the invention, the post-enriched cell population contains at least 1%, 2%, 3%, 4%, 5%, 6%, 7%, 8%, 9%, 10%, 20%, 30%, 40%, 50%, 60%, 70%, 80%, 85%, 90%, 95%, 97%, 98%, 99%, or 100% of the target cell population.

The "CD151" is a four-transmembrane protein, and this protein belongs to the tetraspanin family. CD151 plays an important role in signal transduction involved in cell differentiation, proliferation, and motility. In addition, CD151 is known to form a complex with integrin, thereby participating in functions such as cell adhesion and fusion.

In the invention, CD151 is used as a marker for enriching atrial myocytes or ventricular myocytes in a cardiomyocyte-containing cell population induced from stem cells.

The term "marker" refers to a "marker protein" or "marker gene", and means a protein or a gene thereof expressed specifically on the cell surface, in the cytoplasm, and/or in the nucleus, etc., of a given cell type. The maker may be a positive selection marker or a negative selection marker. The marker is preferably a cell surface marker. The cell surface selection marker may be used to enrich, isolate, and/or detect a viable cell(s).

The marker protein can be detected by utilizing immunological assay, e.g., ELISA, immunostaining, flow cytometry, using an antibody specific to the marker protein. Examples of the marker protein-specific antibody that can be used include an antibody capable of binding to a specific amino acid sequence of the marker protein or to a specific sugar chain linked to the marker protein. Meanwhile, some marker proteins, e.g., a transcription factor or a subunit thereof, may be expressed intracellularly and does not necessarily appear on the cell surface, and in this case, a reporter protein may be expressed together with the marker protein, and the reporter protein may be detected to detect the marker protein of interest. This procedure may be preferably used when a suitable cell surface marker is not detected. The marker gene can be detected by using a nucleic acid amplification method and/or a nucleic acid detection method known in the art, e.g., RT-PCR, microarray, biochip and RNAseq.

The "expression" is defined as transcription of a specific nucleotide sequence driven by a promoter and/or translation of a transcript.

The term "positive" or "expressing" means that a protein or mRNA is expressed at a level that can be detected by a technique known in the art. The protein can be detected by utilizing an immunological assay, e.g., ELISA, immunostaining, flow cytometry, using an antibody. Meanwhile, in the case of proteins, e.g., a transcription factor or a subunit thereof, which may be expressed intracellularly and does not necessarily appear on the cell surface, a reporter protein may be expressed, together with the protein, and the reporter protein may be detected to detect the protein of interest. The mRNA can be detected by using a nucleic acid amplification method and/or a nucleic acid detection method, e.g., RT-PCR, microarray, biochip, and RNAseq.

The term "negative" or "not expressing" means that the expression level of a protein or gene is less than a lower limit of detection by all or any of the above known techniques. The respective techniques may have different detection lower limits of expression of the protein or gene.

The term "pluripotency" means a potential of being able to differentiate into tissues and cells having various different morphologies and functions and a potential of being able to differentiate into any lineage of three embryonic germ layers. The term "pluripotency" which means that it is impossible to differentiate into a blastodisc and an individual cannot be formed, is distinguished from the term "totipotency", which means that it is possible to differentiate into any in vivo tissue including a blastodisc.

The term "multipotency" means a potential of being able to differentiate into a limited number of multiple cell lineages. For example, mesenchymal stem cells, hematopoietic stem cells, and neural stem cells are multipotent but not pluripotent.

The term "culture" refers to cell maintenance, proliferation (growth), and/or differentiation in an in vitro environment. The term "culturing" means maintaining, proliferating (growing), and/or differentiating cells outside a tissue or ex vivo such as on a cell culture dish or plate, or in a flask or culture tank.

The term "maintenance culture (sustain)" means culturing a desired cell population while the number thereof is maintained. The cell number maintenance may be achieved while the cells are viable without proliferation or may be achieved such that an increase in the number of cells due to proliferation matches a decrease in the number of cells due to death. The number of cells is not necessarily maintained such that the number of cells is perfectly the same, and may be maintained such that the number of cells are substantially the same in view of the purpose of the invention.

The term "expansion culture (expand)" means culturing in order to expand a desired cell population and increase the number of cells. The increase in the number of cells may be achieved such that an increase in the number of cells due to proliferation exceeds a decrease in the number of cells due to death, and it is not required that all the cells in the cell population proliferate. The number of cells may be increased by 1.1 fold, 1.2 fold, 1.5 fold, 2 fold, 3 fold, 4 fold, 5 fold, 6 fold, 7 fold, 8 fold, 9 fold, 10 fold, 15 fold, 20 fold, 30 fold, 40 fold, 50 fold, 100 fold, 300 fold, 500 fold, 1000 fold, 3000 fold, 5000 fold, 10000 fold, 100000 fold, or 1000000 fold or more compared with that before the expansion culture starts.

The term "comprise(s) or comprising" refers to inclusion of an element following the term, but is not limited to the element. Thus, the inclusion of an element following the term is suggested, but exclusion of the other optional element(s) is not suggested.

The term "about" or "approximately" indicates a value within an error of ±30%, 25%, 20%, 15%, 10%, 8%, 6%, 5%, 4%, 3%, 2%, or 1% based on a reference value. Preferably, the term "about" or "approximately" indicates a range with an error of ±15%, 10%, 5%, or 1% based on a reference value.

Advantageous Effects of Invention

The invention can provide technology for enriching atrial myocytes or ventricular myocytes in a cardiomyocyte-containing cell population induced from stem cells.

DESCRIPTION OF EMBODIMENTS

Detailed Description of the Invention

Figure 1:
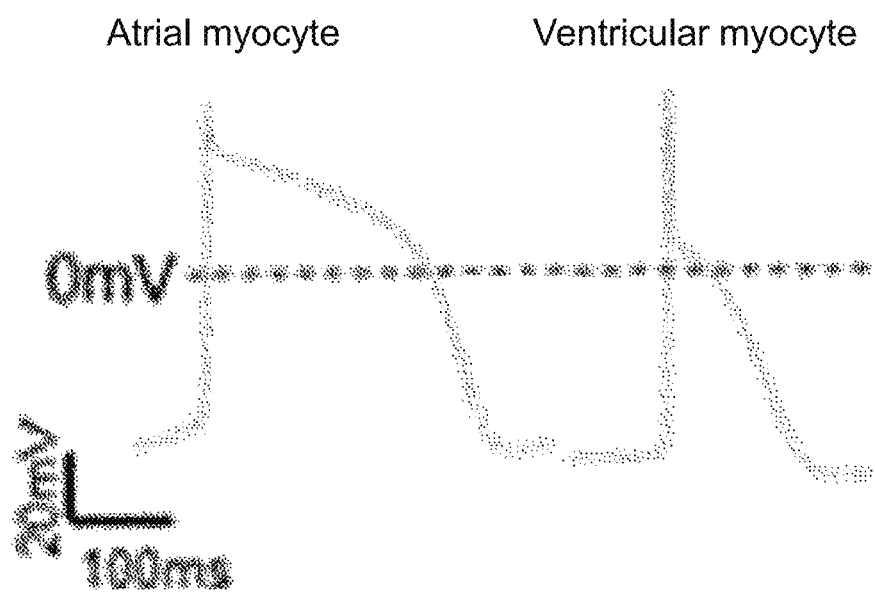
FIG. 1 is a chart showing a representative action potential waveform exhibited by a ventricular myocyte and an atrial myocyte.

Hereinafter, preferred embodiments of the invention will be described. Note that the below-described embodiments are representative examples of the embodiments of the invention. The scope of the invention should not be narrowly construed due to them.

1. Method for Enriching Atrial Myocytes or Ventricular Myocytes in a Cardiomyocyte-containing Cell Population Induced From Stem Cells A method for enriching atrial myocytes or ventricular myocytes according to the invention includes the following step:

(1) Step of collecting atrial myocytes or ventricular myocytes from a cardiomyocyte-containing cell population by using an expression level of CD151 as an index.

In the case of enriching atrial myocytes by the method of the invention, step (1) is specifically the following step (1-1):

(1-1) step of collecting CD151 low expressing cells from a cardiomyocyte-containing cell population.

A cell subpopulation identified by CD151-high expression in a cardiomyocyte-containing cell population induced from stem cells has a higher percentage of ventricular myocytes than a cell subpopulation identified by CD151-low expression. Thus, atrial myocytes can be enriched in the cell population by removing a cell subpopulation identified by CD151-high expression from a cardiomyocyte-containing cell population induced from stem cells or by collecting a cell subpopulation identified by CD151-low expression from the cardiomyocyte-containing cell population.

On the other hand, in the case of enriching ventricular myocytes by the method of the invention, step (1) is specifically the following step (1-2):

(1-2) step of collecting CD151 high expressing cells from a cardiomyocyte-containing cell population.

A cell subpopulation identified by CD151-high expression in a cardiomyocyte-containing cell population induced from stem cells has a higher percentage of ventricular myocytes than a cell subpopulation identified by CD151-low expression. Thus, ventricular myocytes can be enriched in the cell population by removing a cell subpopulation identified by CD151-low expression from a cardiomyocyte-containing cell population induced from stem cells or by collecting a cell subpopulation identified by CD151-high expression from the cardiomyocyte-containing cell population.

[CD151 Detection Probe]

The expression level of CD151 in a cell can be determined using a CD151 detection probe (hereinafter, simply referred to as a "probe") with binding ability to CD151.

The probe may be, for example, an antibody or nucleic acid (e.g., aptamer). Preferred is an antibody.

The probe is preferably conjugated with an optically, electrically, or magnetically detectable label. In this case, a cell is brought into contact with the probe to optically, electrically, or magnetically detect a signal from the label of the probe bound to CD151, thereby enabling determination of the expression level of CD151 in the cell based on the signal intensity.

In addition, when the probe is, for example, an antibody, a labeled secondary antibody bound to the above antibody may be used to determine the expression level of CD151 in the cell.

The invention also provides a reagent for enriching atrial myocytes or ventricular myocytes in a cardiomyocyte-containing cell population induced from stem cells, the reagent comprising the probe.

Based on the distribution of expression level in the cell population, a certain reference value may be set to the expression level of CD151 in a cell. It is then possible to determine, as a high expresser, a cell in which the expression level is the reference value or higher and, as a low expresser, a cell in which the expression level is less than the reference value. In this case, the reference value may be, for instance, the maximum, mean, median, or mode of the expression level in each cell. Preferred is the maximum. The reference value may be set, if appropriate, depending on a cell enriching rate of interest. It is possible to set a value larger or smaller than the maximum, mean, median, or mode (preferably the maximum) of the expression level in each cell by 1%, 2%, 3%, 4%, 5%, 10%, 15%, 20%, 30%, 40%, 50%, 60%, 70%, 80%, 90%, or 100% or more.

Also, the expression level of CD151 in a cell may be set by using, as a reference value, the expression level in a stem cell to determine, as a high expresser, a cell in which the expression level is the reference value or higher and, as a low expresser, a cell in which the expression level is less than the reference value. In this case, the reference value may be, for instance, the maximum, mean, median, or mode of the expression level in stem cells. Preferred is the maximum. The reference value may be set, if appropriate, depending on a cell enriching rate of interest. It is possible to set a value larger or smaller than the maximum, mean, median, or mode (preferably the maximum) of the expression level in stem cells by 1%, 2%, 3%, 4%, 5%, 10%, 15%, 20%, 30%, 40%, 50%, 60%, 70%, 80%, 90%, or 100% or more.

Alternatively, the expression level of CD151 in a cell may be set by using, as a reference value, the signal intensity of a cell not in contact with a probe (negative control) as measured like in a cell in contact with the probe. It is then possible to determine, as a high expresser, a cell in which the signal intensity is the reference value or higher and, as a low expresser, a cell in which the signal intensity is less than the reference value. The reference value may be set, if appropriate, depending on a cell enriching rate of interest. It is possible to set a value larger or smaller than the maximum, mean, median, or mode (preferably the maximum) of the expression level in the negative control by 1%, 2%, 3%, 4%, 5%, 10%, 15%, 20%, 30%, 40%, 50%, 60%, 70%, 80%, 90%, or 100% or more.

Conventionally known conditions are applicable to collection of a cell subpopulation of interest or removal of an unwanted cell subpopulation. For instance, cell sorting using a flow cytometer is preferably applicable. As an example, cells are first reacted with an anti-CD151 primary antibody. Next, the cells are washed to remove a cell-unbound anti-CD151 primary antibody. Then, the cells are reacted with a fluorescently labeled secondary antibody. Further, the cells are washed to remove the fluorescently labeled secondary antibody unbound to the primary antibody. After that, a flow cytometer is used to measure the fluorescent intensity of each cell. Subsequently, each cell in which the expression level is the above reference value or higher is sorted into a CD151 high expressing cell subpopulation (CD151-high) or each cell in which the expression level is less than the reference value is sorted into a CD151 low expressing cell subpopulation (CD151-low).

2. Cardiomyocyte Population Containing Enriched Atrial Myocytes or Ventricular Myocytes The invention also provides a cell population obtained by the above enrichment method in which atrial myocytes are enriched, or a cell population obtained by the above enrichment method in which ventricular myocytes are enriched.

The percentage of atrial myocytes or ventricular myocytes in the cell population is not particularly limited, and the percentage in the collected target cell subpopulation is higher than the percentage in the original cardiomyocyte-containing cell population induced from stem cells by, for example, 5%, 10%, 20%, 30%, 40%, or 50%, preferably 60%, 70%, 80%, or 90%, more preferably 100%, 150%, 200%, 300%, or 400%, and still more preferably 500% or more. The percentage of atrial myocytes or ventricular myocytes in the atrial myocyte-enriched cell population or the ventricular myocyte-enriched cell population, respectively, is, for example, 5% or higher, 10% or higher, 20% or higher, 30% or higher, 40% or higher, 50% or higher, preferably 60% or higher, 70% or higher, 80% or higher, or 90% or higher, and more preferably 99.5% or higher or 99.9% or higher.

A conventionally known technique may be used to identify each cell as an atrial myocyte or a ventricular myocyte. For example, the following electrophysiological analysis, marker expression analysis, and chemical response analysis may be employed for the identification.

For the identification using electrophysiological analysis, the following (1) to (7) by a patch clamp method, for example, may be used. FIG. 1 shows a representative action potential waveform of a ventricular myocyte and an atrial myocyte.

(1) A cell with an action potential waveform, in which the ratio (APD30/90) of the action potential duration at 30% repolarization (APD30) to the action potential duration at 90% repolarization (APD90) is 0.3 or larger and the maximum upstroke velocity ($dv/dt_{max}$) is 10 or higher, is defined as a ventricular myocyte. By contrast, a cell with an action potential waveform, in which the APD30/90 is less than 0.3 and the $dv/dt_{max}$ is 10 or higher, is defined as an atrial myocyte. In this case, a cell with an action potential waveform, in which the $dv/dt_{max}$ is less than 10 and the spontaneous action potential cycle is 1 s or more, is defined as an immature cardiomyocyte that is classified into neither a ventricular myocyte nor an atrial myocyte (Cell Stem Cell, 2017, 21, 179-194).

(2) A cell with an action potential waveform, in which a value for the action potential duration at 50% repolarization (APD50) or APD90 is significantly long, is defined as a ventricular myocyte, and a cell with an action potential waveform, in which the value is significantly short, is defined as an atrial myocyte (JCI Insight, 2018, 3(12): e99941; Eur. Heart J., 2017, 38, 292-301).

(3) A cell with an action potential waveform, in which a value for the action potential duration at 20% repolarization (APD20), APD50, or APD90 is significantly long and the amplitude of the action potential plateau phase ($APA_{Plat}$) is significantly large, is defined as a ventricular myocyte, and a cell with an action potential waveform, in which the value for APD20, APD50, or APD90 is significantly short and the $APA_{Plat}$ is significantly small, is defined as an atrial myocyte (Stem Cell Reports, 2017 Dec 12, 9(6): 1765-1779).

(4) A cell with an action potential waveform, in which a value for the ratio (APD20/80) of APD20 to the action potential duration at 80% repolarization (APD80) is significantly large, is defined as a ventricular myocyte, and a cell with an action potential waveform, in which the value is significantly small, is defined as an atrial myocyte (JCI Insight, 2018, 3(12): e99941).

(5) A cell with an action potential waveform, in which a value for the rate (APD90/50) of APD90 to APD50 is significantly small, is defined as a ventricular myocyte, and a cell with an action potential waveform, in which the value is significantly large, is defined as an atrial myocyte (Eur. Heart J., 2017, 38, 292-301; Eur. Heart J., 2011, 32, 952-962).

(6) A cell with an action potential waveform, in which the APD90/50 is less than 1.4, is defined as a ventricular myocyte, and a cell with an action potential waveform, in which the APD90/50 is larger than 1.7, is defined as an atrial myocyte. In this case, a cell with an action potential waveform, in which the APD90/50 is 1.4 or more and 1.7 or less, is defined as a pacemaker cell (Eur. Heart J., 2011, 32, 952-962).

(7) A cell with an action potential waveform, in which the plateau phase having a membrane potential change within 20 mV lasts 50 ms or longer, the $dv/dt_{max}$ is larger than 50, the action potential amplitude (APA) is larger than 85 mV, and the APD90/50 is less than 2.3, is defined as a ventricular myocyte. A cell with an action potential waveform, in which the action potential waveform is the same as above except that the plateau phase is absent, is defined as an atrial myocyte. A cell with an action potential waveform, in which the action potential waveform is the same as above except that the plateau phase is absent as well as the APD90/50 exceeds 2.3, is defined as a pacemaker cell (PNAS, 2017, E8372-E8381).

For the identification by marker expression analysis, the expression of a marker protein or a marker gene may be measured, and if a cell expresses an atrial myocyte marker and preferably expresses no ventricular myocyte marker, the cell can be determined as an atrial myocyte. By contrast, if a cell expresses a ventricular myocyte marker and preferably expresses no atrial myocyte marker, the cell can be determined as a ventricular myocyte. Examples of the known atrial myocyte marker gene include KCNA5 (potassium voltage-gated channel subfamily A member 5), KCNJ3 (potassium voltage-gated channel subfamily J member 3), NPPA (natriuretic peptide A), NR2F1 (nuclear receptor subfamily 2 group F member 1), NR2F2 (nuclear receptor subfamily 2 group F member 2), or TBXS (T-Box 5). Examples of the known ventricular myocyte marker gene include HEY2 (Hes related family BHLH transcription factor with YRPW motif 2) or MYL2 (myosin light chain 2).

Note that cardiomyocytes including atrial myocytes and ventricular myocytes means cells expressing at least one marker selected from the group consisting of at least cardiomyocyte troponin (cTNT), αMHC (α myosin heavy chain, MYH6), and βMHC (MYH7). The cTNT gene is, for example, NCBI Accession No. NM_000364 in the case of human, and NM_001130176 in the case of mouse. The αMHC gene is, for example, NCBI Accession No. NM_002471 in the case of human, and NM_001164171 in the case of mouse. The βMHC gene is, for example, NCBI Accession No. NM_000257 in the case of human, and NM_080728 in the case of mouse.

The marker protein can be detected by utilizing immunological assay, e.g., ELISA, immunostaining, flow cytometry, using an antibody specific to the marker protein. The marker gene can be detected by using a nucleic acid amplification method and/or a nucleic acid detection method known in the art, e.g., RT-PCR, microarray, biochip.

For the identification by chemical response analysis, examples include a method of detecting a cell response to an activator or inhibitor for an atrial myocyte- or ventricular myocyte-specific channel. For example, carbachol is an agent for activating an atrial myocyte-specific muscarinic potassium channel ($I_{K,Ach}$) When carbachol is added to a cell, the action potential duration (APD) is shortened only in the atrial myocyte, but the APD is not affected in a ventricular myocyte. Meanwhile, 4-aminopyridine is an agent for blocking an ultra-rapidly activating delayed rectifier potassium channel ($IK_{ur}$). When 4-aminopyridine is added to a cell, the APD20 is prolonged only in the atrial myocyte, but the APD is not affected in a ventricular myocyte (Stem Cell Reports, 2018, 11(6): 1378-1390). A cell response to such an agent may be detected, thereby making it possible to identify whether the cell is either an atrial myocyte or a ventricular myocyte.

3. Process for Producing Atrial Myocytes or Ventricular Myocytes From Stem Cells A process for producing atrial myocytes or ventricular myocytes from stem cells according to the invention includes the following steps:

(A) step of inducing a cardiomyocyte-containing cell population from the stem cells; and (B) step of collecting atrial myocytes or ventricular myocytes from the cell population by using an expression level of CD151 as an index.

In the case of producing atrial myocytes by the production process of the invention, steps (A) and (B) are specifically the following steps (A-1) and (B-1):

(A-1) step of inducing a cardiomyocyte-containing cell population from the stem cells under conditions for differentiation into atrial myocytes; and (B-1) step of collecting CD151 low expressing cells from the cell population.

On the other hand, in the case of producing ventricular myocytes by the production process of the invention, steps (A) and (B) are specifically the following steps (A-2) and (B-2):

(A-2) step of inducing a cardiomyocyte-containing cell population from the stem cells under conditions for differentiation into ventricular myocytes; and (B-2) step of collecting CD151 high expressing cells from the cell population.

[Induction Step]

In step (A), (A-1), or (A-2), a cardiomyocyte-containing cell population is induced from stem cells.

[Stem Cell]

Examples of the "stem cell" include a pluripotent stem cell.

The "pluripotent stem cell" that can be used in the present invention refers to a stem cell with a potential of being able to differentiate into tissues and cells having various distinct in vivo morphologies and functions and with a potential of being able to differentiate into any cell lineage of three embryonic germ layers (endoderm, mesoderm, and ectoderm). Examples include, but are not particularly limited to, an embryonic stem cell (ESC), an embryonic stem cell induced from a clone embryo obtained by nuclear transfer, a germline stem cell, embryonic germ cell, or an induced pluripotent stem cell (herein sometimes referred to as an "iPSC"). In addition, the "multipotent stem cell" that can be used in the present invention refers to a stem cell with a potential of being able to differentiate into a limited number of multiple cell lineages. Examples of the "multipotent stem cell" that can be used in the present invention include a dental pulp stem cell, an oral mucosa-induced stem cell, a hair follicle stem cell, or a somatic stem cell induced from a cultured fibroblast or a bone marrow stem cell. A preferable pluripotent stem cell is an ESC or iPSC.

As the "ESC", examples of an available mouse ESC include various mouse ESC strains established by, for example, inGenious targeting laboratory, Inc., or RIKEN. Examples of an available human ESC include various human ESC strains established by, for example, University of Wisconsin, NIH, RIKEN, Kyoto University, National Center for Child Health and Development, or Cellartis, Inc. Examples of the available human ESC strain include: CHB-1 to CHB-12 strains, RUES1 strain, RUES2 strain, HUES1 to HUES28 strains distributed by ESI Bio, Inc.; H1 strain, H9 strain distributed by WiCell Research; or KhES-1 strain, KhES-2 strain, KhES-3 strain, KhES-4 strain, KhES-5 strain, SSES1 strain, SSES2 strain, or SSES3 strain distributed by RIKEN.

The "induced pluripotent stem cell" refers to a cell obtained by introducing specific factors (nuclear reprogramming factors) into a mammalian somatic cell or undifferentiated stem cell for reprogramming. Various "induced pluripotent stem cells" are currently available. Examples of the stem cell that can be used include: an iPSC established by introducing 4 factors: Oct3/4, Sox2, Klf4, and c-Myc into a mouse fibroblast by Yamanaka and colleagues (Takahashi K, Yamanaka S., Cell, (2006) 126: 663-676); a human cell-induced iPSC established by introducing the same 4 factors into a human fibroblast (Takahashi K, Yamanaka S., et al., Cell, (2007) 131: 861-872); a Nanog-iPSC established by introducing the above 4 factors and then selecting while using the Nanog expression as a marker (Okita, K., Ichisaka, T., and Yamanaka, S. (2007), Nature 448, 313-317); an iPSC produced by a c-Myc-free protocol (Nakagawa M, Yamanaka S., et al., Nature Biotechnology, (2008) 26, 101-106); or an iPSC established by introducing 6 factors by a virus-free protocol (Okita K et al., Nat. Methods, 2011 May, 8(5): 409-12; Okita K et al., Stem Cells, 31(3): 458-66). Additional examples include: an induced pluripotent stem cell that was established by introducing 4 factors: OCT3/4, SOX2, NANOG, and LIN28 and was produced by Thomson and colleagues (Yu J., Thomson J A. et al., Science (2007), 318: 1917-1920); an induced pluripotent stem cell produced by Daley and colleagues (Park I H, Daley G Q. et al., Nature (2007) 451: 141-146); or an induced pluripotent stem cell produced by Sakurada, et al. (JP-A-2008-307007).

In addition, it is possible to use any of induced pluripotent stem cells known in the art and described in any of published research articles (e.g., Shi Y., Ding S., et al., Cell Stem Cell, (2008) Vol3, Issue 5, 568-574; Kim J B., Scholer H R., et al., Nature, (2008) 454, 646-650; Huangfu D., Melton, D A., et al., Nature Biotechnology, (2008) 26, No 7, 795-797) or any of patents (e.g., JP-A-2008-307007, JP-A-2008-283972, US2008-2336610, US2009-047263, WO2007-069666, WO2008-118220, WO2008-124133, WO2008-151058, WO2009-006930, WO2009-006997, WO2009-007852).

As the induced pluripotent stem cell line, various iPSC strain established by, for example, NIH, RIKEN, or Kyoto University is available. Examples of the human iPSC strain include: HiPS-RIKEN-1A strain, HiPS-RIKEN-2A strain, HiPS-RIKEN-12A strain, Nips-B2 strain distributed by RIKEN; or 253G1 strain, 201B7 strain, 409B2 strain, 454E2 strain, 606A1 strain, 610B1 strain, 648A1 strain, 1231A3 strain, 1390D4 strain, and 1390C1 strain distributed by Kyoto University. More preferred is 1390D4 strain or 1390C1 strain. Alternatively, it is possible to use, for instance, a clinical-grade cell strain provided by Kyoto University or Cellular Dynamics International or cell lines for research or clinical purpose produced using the above cell strain.

[Conditions for Differentiation into Atrial Myocyte]

The conditions for differentiation into atrial myocyte which can be used may be conventionally known conditions (see, for example, EMBO Mol Med (2015), 7: 394-410). For example, an embryoid body produced from an iPSC is cultured for 2 days in a basal medium containing BMP4, activin A, and bFGF, and then cultured for 3 days in a basal medium containing VEGF, Wnt inhibitor, TGF-β inhibitor, and retinoic acid. Further, a VEGF-containing basal medium may be used for culture to produce a cell population containing atrial myocytes.

The differentiation induction period is not particularly limited, and is, for instance, from 7 to 40 days or, depending on the purpose, 120 days, 90 days, 60 days, 30 days, 28 days, 21 days, 14 days, or 7 days.

[Conditions for Differentiation into Ventricular Myocyte]

The conditions for differentiation into ventricular myocyte which can be used may be conventionally known conditions (see, for example, Cell Stem Cell. (2011), 8(2): 228-40). For example, an embryoid body produced from an iPSC is cultured for 2 days in a basal medium containing BMP4, activin A, and bFGF, and then cultured for 3 days in a basal medium containing VEGF, Wnt inhibitor, BMP4 inhibitor, and TGF-β inhibitor. Further, a VEGF-containing basal medium may be used for culture to produce a cell population containing ventricular myocytes.

The differentiation induction period is not particularly limited, and is, for instance, from 7 to 40 days or, depending on the purpose, 120 days, 90 days, 60 days, 30 days, 28 days, 21 days, 14 days, or 7 days.

Preferred examples of the basal medium include, but are not particularly limited to, StemPro-34 SFM (ThermoFisher), STEMdiff APEL2 culture medium (STEMCELL Technologies, ST-05275), TeSR1 culture medium, and Chemically Defined Medium (CDM). Additional examples of the medium that can be used include BME culture medium, BGJb culture medium, CMRL 1066 culture medium, Glasgow MEM culture medium, Improved MEM (IMEM) culture medium, Improved MDM (IMDM) culture medium, Medium 199 culture medium, Eagle MEM culture medium, aMEM culture medium, DMEM culture medium (high glucose or low glucose), DMEM/F12 culture medium, Ham culture medium, RPMI 1640 culture medium, Fischer's culture medium, and a mixed culture medium thereof.

Examples of the CDM culture medium that can be used include, but are not particularly limited to, a culture medium prepared from Iscove's modified Dulbecco's medium (GE Healthcare, Inc.).

The basal medium may contain a substance(s) routinely used for cell culture, such as Ham's F-12 nutrient mixture, albumin such as human serum albumin, polyvinyl alcohol (PVA), deionized BSA, linoleic acid, linolenic acid, cholesterol, insulin, apotransferrin, selenium, ethanolamine, monothioglycerol, protein-free hybridoma mixture II (PFH-MII), ascorbic acid, L-alanyl-L-glutamine, and/or an antibiotic.

The Wnt inhibitor (Wnt signal inhibitor) used is a substance of inhibiting a Wnt-mediated signaling pathway, and examples include IWP-2, IWP-3, IWP-4, 2-(4-trifluoromethylphenyl)-7,8-dihydro-5H-thiopyrano[4,3-d]pyrimidin-4 (3H)-one, IWR1, G-CSF, IGFBP4, Dkk1, Cerberus, an anti-Wnt antibody, a Wnt agonist (Wnt receptor inhibitor), a soluble Wnt receptor protein (e.g., Frzb-1), or a dominant negative molecule. Two or more of these substances may be used in combination.

Examples of the BMP4 inhibitor that can be used include dorsomorphin (6-[4-(2-piperidin-1-yletoxy)phenyl]-3-pyridin-4-ylpyrazolo[1,5-A]pyrimidine), indirubin-3'-oxime, phenformin HCl, GSK621, WZ4003, or HTH-01-015. Two or more of these substances may be used in combination.

Examples of the TGF-β inhibitor include SB431542 (4-[4-(1,3-benzodioxol-5-yl)-5-(2-pyridinyl)-1H-imidazol-2-yl]-benzamide), A83-01 (4-[4-(1,3-benzodioxol-5-yl)-5-(2-pyridinyl)-1H-imidazol-2-yl]-benzamide), LDN193189 (4-[6-[4-(1-piperazinyl)phenyl]pyrazolo[1,5-a]pyrimidin-3-yl]-quinoline), GW788388 (4-[4-[3-(2-pyridinyl)-1H-pyrazol-4-yl]-2-pyridinyl]-N-(tetrahydro-2H-pyran-4-yl)-benzamide), SM16 (4-[4-(1,3-benzodioxol-5-yl)-5-(6-methyl-2-pyridinyl)-1H-imidazol-2-yl]-bicyclo[2.2.2]octane-1-carboxamide), IN-1130 (3-[[5-(6-methyl-2-pyridinyl)-4-(6-quinoxalinyl)-1H-imidazol-2-yl]methyl]-benzamide), GW6604 (2-phenyl-4-[3-(pyridin-2-yl)-1H-pyrazol-4-yl]pyridine), and SB505124 (2-[4-(1,3-benzodioxol-5-yl)-2-(1,1-dimethylethyl)-1H-imidazol-5-yl]-6-methyl-pyridine). Two or more of these substances may be used in combination.

[Separation Step]

In step (B), (B-1), or (B-2), atrial myocytes or ventricular myocytes are collected from the resulting cell population by using the expression level of CD151 as an index.

This step is like in the method for enriching atrial myocytes or ventricular myocytes as described above.

4. Atrial Myocytes and Ventricular Myocytes

The invention also provides a cell population obtained by the above production process, in which atrial myocytes or ventricular myocytes are enriched.

[Pharmaceutical]

The cell population, atrial myocytes, or ventricular myocytes according to the invention are applicable to a cell pharmaceutical that comprises the above cells and is used for heart disease therapy or a method of treating heart disease by administering the cell pharmaceutical. In addition, the invention provides use of the cell population, atrial myocytes, or ventricular myocytes for the manufacture of the cell pharmaceutical, or the cell population, atrial myocytes, or ventricular myocytes for use in treatment of heart disease.

The cell pharmaceutical may be used for regenerative medicine of heart disease, such as myocardial infarction, heart failure, ischemic heart disease, cardiomyopathy, myocarditis, hypertrophic cardiomyopathy, dilated phase hypertrophic cardiomyopathy, or dilated cardiomyopathy.

Cells included in the cell pharmaceutical may be, for instance, cells collected by scraping cells during culturing or cells frozen in a cryopreservation liquid. Cells that are in the same lot and can be obtained by expansion culture may be aliquoted, and then frozen and stored, which is preferable from the viewpoint of stably exerting substantially the same effects, excellent handling, and so on.

The cell pharmaceutical may be provided in any form, such as a suspension obtained by suspending cells in a suitable solvent, a cell aggregate, and a monolayer or multilayer cell sheet. The solvent used may be water, saline, or various buffer or cell preservation liquid. Also, the cell aggregate and cell sheet may consist of cells or may include a suitable biocompatible material and cells. Examples of the biocompatible material include collagen, polyglycolic acid (PGA), polylactic acid, alginate, polyethylene oxide, a polylactic acid-polyglycolic acid copolymer, proteoglycan, glycosaminoglycan, human derma, or a combination thereof. The biocompatible material may be a film (e.g., a sheet), a porous body (e.g., a sponge), or a mesh (e.g., a woven fabric, cloth, and nonwoven fabric).

The cell pharmaceutical optionally contains an additional component(s) such as a pharmaceutically acceptable carrier or an additive, depending on the application and the form according to a common procedure. Examples of the carrier or additive include a tonicity agent, a thickener, sugar, a sugar alcohol compound, an antiseptic (preservative), a bactericide or antibacterial agent, a pH modifier, a stabilizer, a chelator, an oil base, a gel base, a surfactant, a suspending agent, a fluidizing agent, a dispersant, a buffering agent, or an antioxidant.

The cell pharmaceutical is used to provide a method of treating the above disease, the method comprising administering to a patient a therapeutically effective amount of the cell pharmaceutical.

The therapeutically effective amount refers to an amount of cells used to elicit a therapeutic effect on the above disease in the case of administering the cells to a patient when compared to the control without administration. The specific therapeutically effective amount may be set, if appropriate, depending on the dosage form, the administration method, usage, and the age, body weight, and symptom of the patient. The effective human (e.g., adult) dose per therapy may be, for example, 200,000 to 1,000,000 cells/kg body weight.

Examples of the cell pharmaceutical administration method include intraperitoneal injection, subcutaneous injection, intra-lymph node injection, intravenous injection, intrathoracic injection, or local direct injection by laparotomy.

[Frozen Stock]

The invention also provides a frozen stock containing a cell population and/or atrial myocytes and/or ventricular myocytes obtained by this step.

The frozen stock may be produced by separating the resulting cell population and/or atrial myocytes and/or ventricular myocytes from a culture medium by centrifugation and then suspending and freezing them in a cryopreservation liquid. The cryopreservation liquid used may be a conventional reagent used for cryopreservation of cells. Examples of the commercially available product include Cryostem Freezing Medium (trade name) and CELLBANKER (registered trademark).

The frozen stock may be used for preparation of, for instance, a tissue model (artificial heart) including, as components, atrial myocytes and ventricular myocytes.

EXAMPLES

Test Example 1

Induction of Cardiomyocyte Population From iPSCs

A cardiomyocyte-containing cell population was induced from iPSCs under conditions for differentiation into atrial myocytes or conditions for differentiation into ventricular myocytes.

The iPSCs used were a double knock-in human iPS cell line (1390D4 strain) in which a reporter protein EmGFP was inserted in the TNNI1 locus and a reporter protein mCherry was inserted in the TNNI3 locus.

The iPSCs were maintained and cultured in accordance with a conventionally known protocol ("An Efficient Non-viral Method to Generate Integration-Free Human-Induced Pluripotent Stem Cells from Cord Blood and Peripheral Blood Cells", Stem Cells, 2012).

The iPSCs were seeded on a low-adherent 6-well plate ($2 \times 10^6$ cells/1.5 ml/well), and were subject to static culture at 37° C. under 5% oxygen conditions to form an embryoid body (day 0). The culture medium used was StemPro-34 SFM (ThermoFisher) containing 1% L-glutamine, 150

µg/mL transferrin, 50 µg/mL ascorbic acid, $4\times10^{-4}$ M monothioglycerol, 10 µM Rock inhibitor (Y-27632), 2 ng/mL BMP4, and 0.5% Matrigel.

[Conditions for Differentiation into Atrial Myocyte]

Next day (day 1), 1.5 ml/well of atrial myocyte induction medium 1 was added to each well containing the cells seeded, and the mixture was cultured at 37° C. under 5% oxygen conditions for additional 2 days. The atrial myocyte induction medium 1 used was StemPro-34 SFM containing 1% L-glutamine, 150 µg/mL transferrin, 50 µg/mL ascorbic acid, $4\times10^{-4}$ M monothioglycerol, 4 ng/mL BMP4, 8 ng/ml activin A, and 10 ng/ml bFGF.

Subsequently (day 3), the culture medium was changed to atrial myocyte induction medium 2, and the mixture was cultured at 37° C. under 5% oxygen conditions for 3 days. The atrial myocyte induction medium 2 used was StemPro-34 SFM containing 1% L-glutamine, 150 µg/mL transferrin, 50 µg/mL ascorbic acid, $4\times10^{-4}$ M monothioglycerol, 10 ng/ml VEGF, 1 µM Wnt inhibitor (IWP-3), 5.4 µM TGF-β inhibitor (SB431542), and 1 µM retinoic acid.

[Conditions for Differentiation into Ventricular Myocyte]

Next day (day 1), 1.5 ml/well of ventricular myocyte induction medium 1 was added to each well containing the cells seeded, and the mixture was cultured at 37° C. under 5% oxygen conditions for additional 2 days. The ventricular myocyte induction medium 1 used was StemPro-34 SFM containing 1% L-glutamine, 150 µg/mL transferrin, 50 µg/mL ascorbic acid, $4\times10^{-4}$ M monothioglycerol, 18 ng/mL BMP4, 12 ng/ml activin A, and 10 ng/ml bFGF.

Subsequently (day 3), the culture medium was changed to ventricular myocyte induction medium 2, and the mixture was cultured at 37° C. under 5% oxygen conditions for 3 days. The ventricular myocyte induction medium 2 used was StemPro-34 SFM containing 1% L-glutamine, 150 µg/mL transferrin, 50 µg/mL ascorbic acid, $4\times10^{-4}$ M monothioglycerol, 10 ng/ml VEGF, 1 µM Wnt inhibitor (IWP-3), 0.6 µM BMP4 inhibitor (Dorsomorphin), and 5.4 µM TGF-inhibitor (SB431542).

[Common Manipulation]

On day 6, under conditions for differentiation into the ventricular myocyte or atrial myocyte, the culture medium was changed to cardiomyocyte induction medium 3, and the mixture was cultured at 37° C. under 5% oxygen conditions for 14 days to produce a cell population containing ventricular myocytes or atrial myocytes (day 20). The cardiomyocyte induction medium 3 used was StemPro-34 SFM containing 1% L-glutamine, 150 µg/mL transferrin, 50 µg/mL ascorbic acid, $4\times10^{-4}$ M monothioglycerol, and 5 ng/ml VEGF. The culture medium was changed at days 8, 10, 13, 15, and 17. After the medium change at day 10, the cells were cultured under regular oxygen conditions.

Test Example 2

Sorting a Cardiomyocyte Population Based on the Expression Level of CD151

A cell population containing atrial myocytes or ventricular myocytes on culture day 20 was dispersed into single cells, and the number of the cells was counted.

An anti-CD151 antibody (BD) was added to the cell suspension, and the mixture was allowed to stand at 4° C. for 30 min. An antibody-free sample was also prepared as a negative control.

After washing, an Alexa (registered trademark) 647-labeled secondary antibody was added to the cell suspension, and the mixture was allowed to stand at 4° C. for 30 min.

Figure 2:
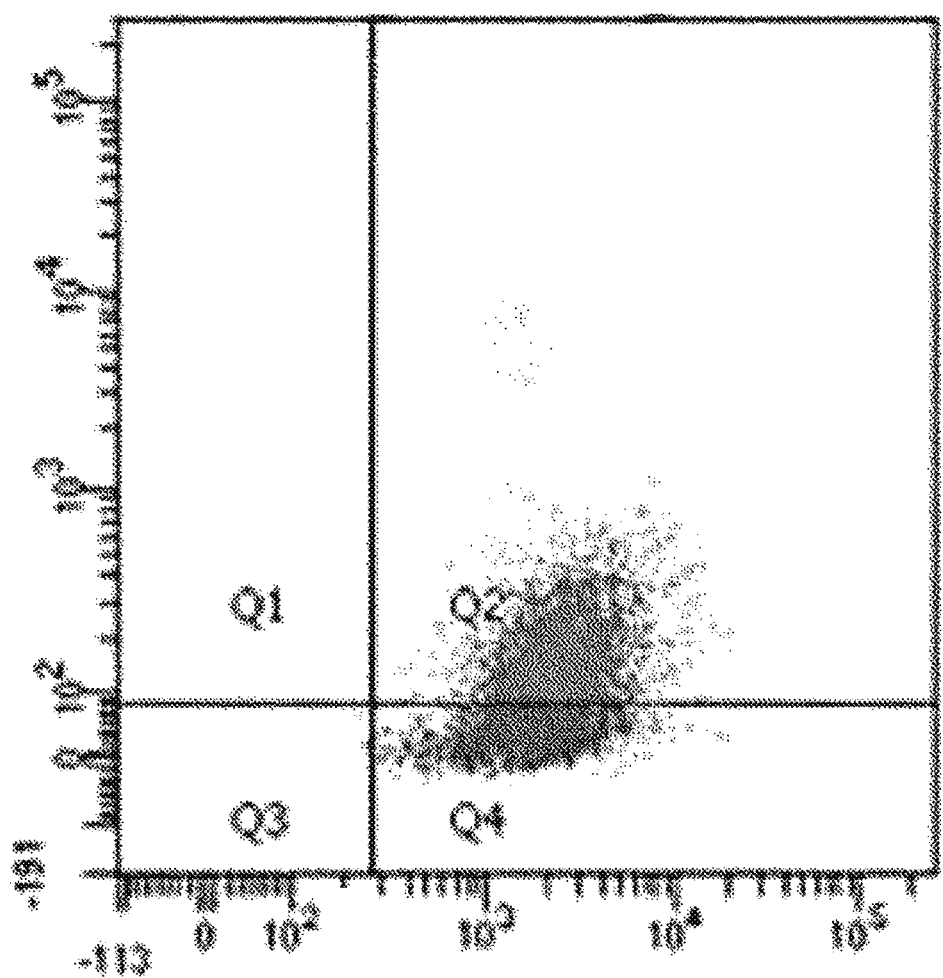
FIG. 2 shows the results of analyzing, by flow cytometry, the expression of CD151 in a cardiomyocyte-containing cell population induced from iPSCs under ventricular myocyte induction conditions. The abscissa represents the fluorescent intensity of EmGFP, and the ordinate represents the fluorescent intensity of Alexa (registered trademark) 647. In the figure, "Q2" indicates a "CD151-high" cell subpopulation, and "Q4" indicates a "CD151-low" cell subpopulation.
Figure 3:
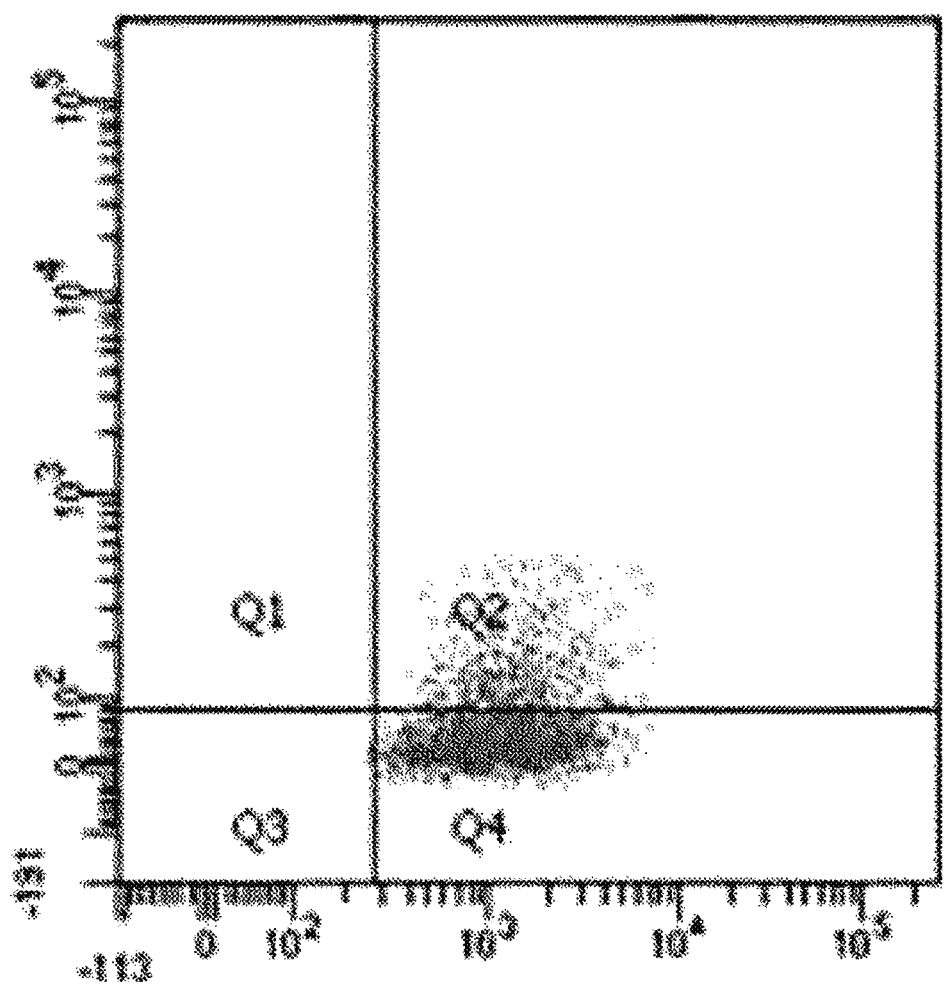
FIG. 3 shows the results of analyzing, by flow cytometry, the expression of CD151 in a cardiomyocyte-containing cell population induced from iPSCs under atrial myocyte induction conditions. The abscissa represents the fluorescent intensity of EmGFP, and the ordinate represents the fluorescent intensity of Alexa (registered trademark) 647. In the figure, "Q2" indicates a "CD151-high" cell subpopulation and "Q4" indicates a "CD151-low" cell subpopulation.

A flow cytometer (BD FACSAria Fusion cell sorter) was used to analyze the expression of CD151 in each EmGFP-positive cell. The "CD151-low" was defined as a cell subpopulation exhibiting a fluorescent intensity less than the maximum fluorescent intensity of negative control cells. The "CD151-high" was defined as a cell subpopulation exhibiting a fluorescent intensity higher than that of the negative control. Each cell subpopulation was sorted. FIGS. 2 and 3 show a flow cytometry plot, and Table 1 shows the percentage of each cell subpopulation.

TABLE 1

|  | CD151-high | CD151-low |
| --- | --- | --- |
| Conditions for differentiation into ventricular myocytes | 55.4% | 44.5% |
| Conditions for differentiation into atrial myocytes | 24.7% | 75.0% |

Test Example 3

Determining the Percentage of Atrial Myocytes or Ventricular Myocytes in "CD151-Low" or "CD151-High" Cell Subpopulation The "CD151-high" or "CD151-low" cell subpopulation was obtained under conditions for differentiation into ventricular myocytes or conditions for differentiation into atrial myocytes, respectively. The percentage of atrial myocytes or ventricular myocytes was determined using an electrophysiological technique.

Each cell subpopulation was cultured on a cover glass coated with fibronectin. StemPro-34 SFM containing 1% L-glutamine, 150 µg/mL transferrin, 50 µg/mL ascorbic acid, $4\times10^{-4}$ M monothioglycerol, and 5 ng/ml VEGF was used for culture. The culture medium was changed every 3 days, and the cells were cultured at 37° C. under regular oxygen conditions. The cells at culture days 13 to 16 were subjected to electrophysiological analysis. A whole cell patch clamp technique using an Axopatch 200B amplifier (Molecular Devices) and pCLAMP software was used for analysis. An electrode was prepared using a glass capillary (WPI) and a micropipette puller, and then filled with an intracellular solution (130 mM KOH, 130 mM L-Aspartic acid, 20 mM KCl, 5 mM NaCl, 10 mM HEPES, 5 mM Mg-ATP, 10 mM EGTA, 1 mM $MgCl_2$, pH 7.2). While Gey's balanced salt solution (Sigma) as an extracellular solution was circulated, the experiments were conducted at 35 to 37° C. A spontaneous action potential of each cell was recorded in a current clamp mode for 1 min. The APD30, APD90, and maximum upstroke velocity ($dv/dt_{max}$) were calculated from the waveform obtained by averaging contiguous 8 to 10 morphologies. A cell with a morphology in which APD30/90≥0.3 and $dv/dt_{max}$≥10 was defined as a ventricular myocyte, and a cell with a morphology in which APD30/90≥0.3 and $dv/dt_{max}$≥10 was defined as an atrial myocyte. Cells with a morphology in which $dv/dt_{max}$<10 were classified into other cells.

Table 2 shows the results.

TABLE 2

|  | Conditions for differentiation into ventricular myocytes | | Conditions for differentiation into atrial myocytes | |
| --- | --- | --- | --- | --- |
|  | CD151-high (n = 17) | CD151-low (n = 21) | CD151-high (n = 16) | CD151-low (n = 16) |
| Ventricular myocytes (%) | 94.1 | 71.4 | 18.8 | 56.3 |
| Atrial myocytes (%) | 0.0 | 23.8 | 0.0 | 37.5 |
| Other cells (%) | 5.9 | 4.8 | 81.3 | 6.3 |

The "CD151-high" cell subpopulation obtained under conditions for differentiation into ventricular myocytes contained ventricular myocytes at a high percentage (94.1%). The "CD151-low" cell subpopulation obtained under conditions for differentiation into ventricular myocytes included many ventricular myocytes (71.4%), but contained a certain number of atrial myocytes (23.8%). It is thus clear that the "CD151-low" cell subpopulation (containing ventricular myocytes at 71.4% and atrial myocytes at 23.8%) should be removed from a population containing all the cells obtained under conditions for differentiation into ventricular myocytes or the "CD151-high" cell subpopulation should be collected therefrom to produce a cell population containing enriched ventricular myocytes.

Meanwhile, the "CD151-low" cell subpopulation obtained under conditions for differentiation into atrial myocytes contained atrial myocytes at a relatively high percentage (37.5%). Also, the "CD151-high" cell subpopulation obtained under conditions for differentiation into atrial myocytes included no atrial myocytes, but contained a certain number of ventricular myocytes (18.8%). It is thus clear that the "CD151-high" cell subpopulation (containing ventricular myocytes at 18.8%) should be removed from a population containing all the cells obtained under conditions for differentiation into atrial myocytes or the "CD151-low" cell subpopulation should be collected therefrom to produce a cell population containing enriched atrial myocytes.

Test Example 4

Analyzing Expression of Each Atrial Myocyte Marker and Ventricular Myocyte Marker in "CD151-High" and "CD151-Low" Cell Subpopulation The "CD151-high" cell subpopulation was obtained under conditions for differentiation into ventricular myocytes and the "CD151-low" cell subpopulation was obtained under conditions for differentiation into atrial myocytes in Test Example 2. Then, the level of expression of each ventricular myocyte marker or atrial myocyte marker was analyzed.

Figure 4:
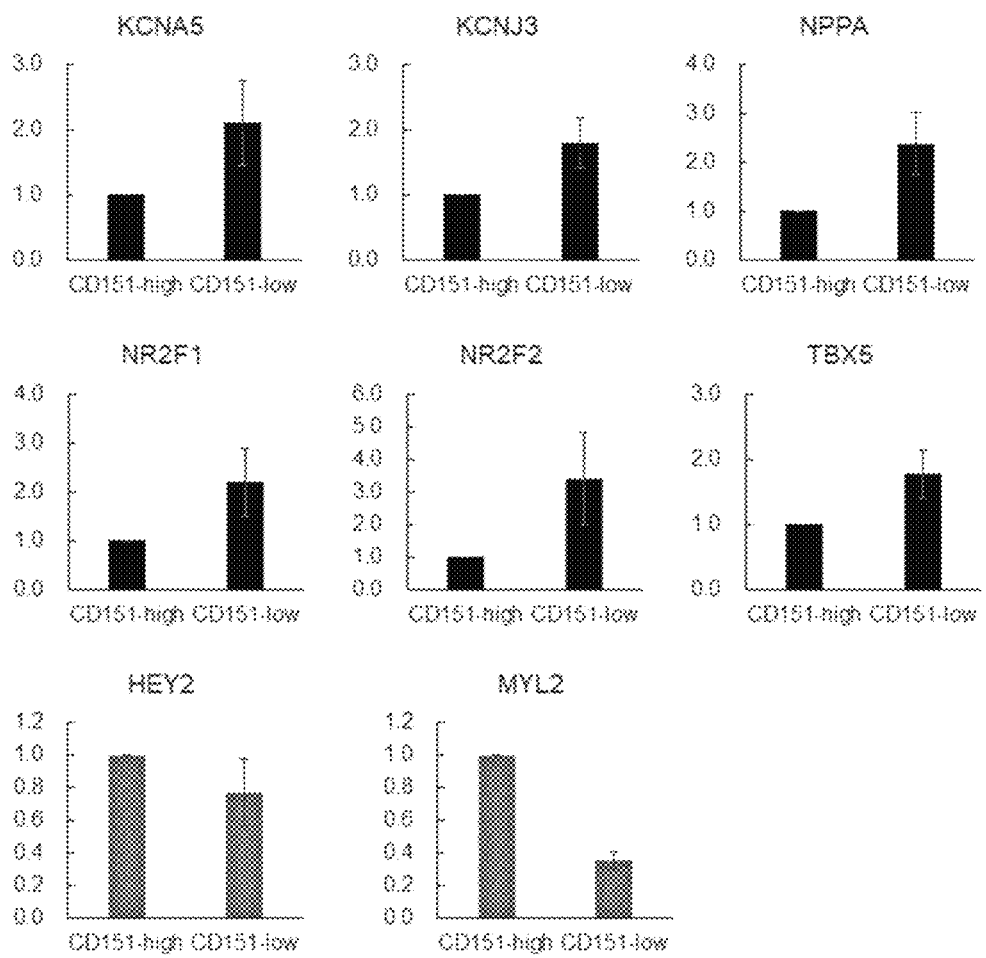
FIG. 4 is graphs indicating the expression level of an atrial myocyte marker gene (KCNA5, KCNJ3, NPPA, NR2F1, NR2F2, TBX5) and a ventricular myocyte marker gene (HEY2, MYL2) for a "CD151-low" cell subpopulation obtained under conditions for differentiation into atrial myocytes and a "CD151-high" cell subpopulation obtained under conditions for differentiation into ventricular myocytes. The expression level of each atrial myocyte marker gene is represented by a relative value (mean ±standard error) while the expression level in the "CD151-high" cell subpopulation obtained under conditions for differentiation into atrial myocytes is set to 1. The expression level of each ventricular myocyte marker gene is represented by a relative value (mean±standard error) while the expression level in the "CD151-high" cell subpopulation obtained under conditions for differentiation into ventricular myocytes is set to 1.

Total RNA was extracted from each cell subpopulation in accordance with a common procedure. Then, the level of expression of an atrial myocyte marker gene (KCNA5, KCNJ3, NPPA, NR2F1, NR2F2, or TBX5) or a ventricular myocyte marker gene (HEY2 or MYL2) was analyzed. FIG. 4 show the results. The expression level of the atrial myocyte marker gene is the expression level of each marker in cells obtained under conditions for differentiation into atrial myocytes, and is represented by a relative value (mean±standard error) while the expression level in the "CD151-high" cell subpopulation obtained under conditions for differentiation into atrial myocytes is set to 1. The expression level of the ventricular myocyte marker gene is the expression level of each marker in cells obtained under conditions for differentiation into ventricular myocytes, and is represented by a relative value (mean±standard error) while the expression level in the "CD151-high" cell subpopulation obtained under conditions for differentiation into ventricular myocytes is set to 1.

The expression of each atrial myocyte marker gene was found to be higher in the "CD151-low" cell subpopulation obtained under conditions for differentiation into atrial myocytes than in the "CD151-high" cell subpopulation. It is thus clear that the "CD151-high" cell subpopulation should be removed from a population containing all the cells obtained under conditions for differentiation into atrial myocytes or the "CD151-low" cell subpopulation should be collected therefrom to produce a cell population containing enriched atrial myocytes.

The expression of each ventricular myocyte marker gene was found to be higher in the "CD151-high" cell subpopulation obtained under conditions for differentiation into ventricular myocytes than in the "CD151-low" cell subpopulation. It is thus clear that the "CD151-low" cell subpopulation should be removed from a population containing all the cells obtained under conditions for differentiation into ventricular myocytes or the "CD151-high" cell subpopulation should be collected therefrom to produce a cell population containing enriched ventricular myocytes.

In Test Examples 1 to 4, used was a double knock-in human iPS cell line 1390D4 in which a reporter protein EmGFP was inserted in the TNNI1 locus and a reporter protein mCherry was inserted in the TNNI3 locus. Here, similar results were obtained in a test using a human iPS cell line 1390C1.

Test Example 5

Identifying a Cell Subtype by Using an Atrial Myocyte-Specific Channel Inhibitor or Activator in a "CD151-High" or "CD151-Low" Cell Subpopulation The "CD151-high" cell subpopulation was obtained under conditions for differentiation into ventricular myocytes and the "CD151-low" cell subpopulation was obtained under conditions for differentiation into atrial myocytes in Test Example 2. Then, their response to an atrial monocyte-specific channel inhibitor 4-aminopyridine or activator carbachol was analyzed.

Each cell subpopulation was seeded at $5\times10^4$ cells/5 μL and cultured on a glass-bottom dish coated with fibronectin. StemPro-34 SFM containing 1% L-glutamine, 150 μg/mL transferrin, 50 μg/mL ascorbic acid, $4\times10^{-4}$ M monothioglycerol, and 5 ng/ml VEGF was used. The culture medium was changed every 3 days, and the cells were cultured at 37° C. under regular oxygen conditions. The cells at culture days 6 to 10 were subjected to membrane potential analysis.

First, the culture medium was removed. Next, 0.2 μL of membrane potential sensitive dye (FluoVolt, ThermoFisher scientific, F10488) was added per 200 μL of Gey's balanced salt solution (Sigma). Then, the resulting solution was added dropwise onto a glass portion of the dish where the cells were seeded. Subsequently, the cells were incubated at 37° C. under regular oxygen conditions for 15 min. After the membrane potential dye-containing solution was removed, 1 mL of Gey's balanced salt solution was added to the dish. The dish was incubated for 1 h in an incubator (at 37° C. under regular oxygen conditions) on a microscope stage. Each "CD151-high"-induced cell was analyzed under 1 Hz pacing, and each "CD151-low"-induced cell was analyzed under 3 Hz pacing.

An AquaCosmos2.6 (Hamamatsu Photonics K. K.) was used for the analysis. While each cell was irradiated with excitation light at 490 nm every 5.9 ms for 20 s, the fluorescence response was measured. The measurement area (ROI) was set to 512×64 pixels.

How addition of 4-aminopyridine affected an action potential was examined. For this purpose, an action potential waveform before the chemical addition was first acquired. Next, 4-aminopyridine (at a final concentration of 50 μM; Sigma) was added to the dish. Then, the dish was allowed to stand for 10 min. After that, an action potential waveform in the same ROI was obtained.

How addition of carbachol affected an action potential was examined. For this purpose, an action potential waveform before the chemical addition was first acquired. Next, carbachol (at a final concentration of 10 μM; Sigma) was added to the dish. Then, the dish was allowed to stand for 1 min. After that, an action potential waveform in the same ROI was obtained.

Figure 5:
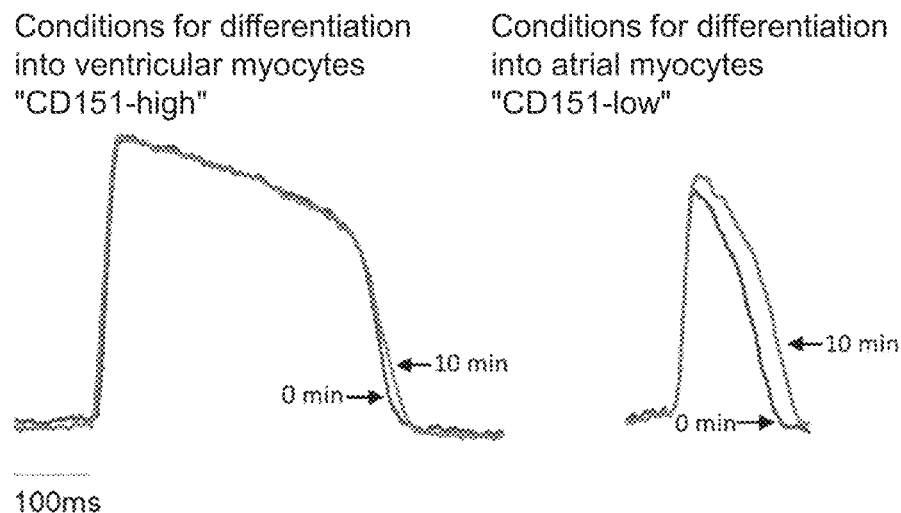
FIG. 5 is graphs indicating a response of the "CD151-high" cell subpopulation obtained under conditions for differentiation into ventricular myocytes and the "CD151-low" cell subpopulation obtained under conditions for differentiation into atrial myocytes to an inhibitor and an activator of atrial myocyte-specific channel. (A) demonstrates the response to the inhibitor (4-aminopyridine), and (B) demonstrates the response to the activator (carbachol).
Figure 5:
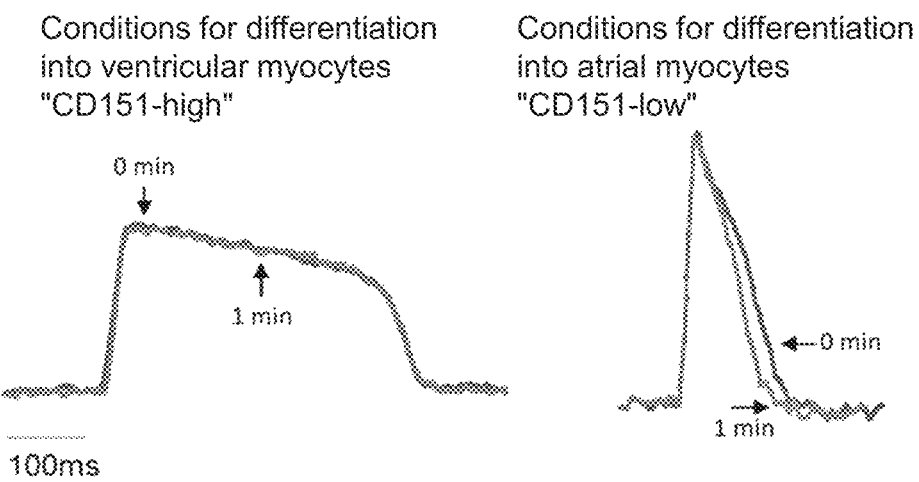

Contiguous 6 to 10 morphologies were averaged to give an action potential waveform of interest. FIG. 5 shows each waveform before or after addition of 4-aminopyridine or carbachol.

The 4-aminopyridine addition was found to prolong the action potential duration (APD) in the "CD151-low" cell subpopulation obtained under conditions for differentiation into atrial myocytes. By contrast, little APD extension was found in the "CD151-high" cell subpopulation obtained under conditions for differentiation into ventricular myocytes (see FIG. 5(A)).

In addition, the carbachol addition was found to shorten the APD in the "CD151-low" cell subpopulation obtained under conditions for differentiation into atrial myocytes. By contrast, no APD change was found in the "CD151-high" cell subpopulation obtained under conditions for differentiation into ventricular myocytes (see FIG. 5(B)).

The above chemical responses have demonstrated that the "CD151-low" cell subpopulation obtained under conditions for differentiation into atrial myocytes corresponds to atrial myocytes and the "CD151-high" cell subpopulation obtained under conditions for differentiation into ventricular myocytes corresponds to ventricular myocytes.

The invention claimed is:

1. A method for enriching atrial myocytes or ventricular myocytes in a cardiomyocyte-containing cell population induced from stem cells, comprising a step of enriching atrial myocytes by removing a cell subpopulation identified by CD151-high expression from the cardiomyocyte-containing cell population or by collecting a cell subpopulation identified by CD151-low expression from the cardiomyocyte-containing cell population, or enriching ventricular myocytes by removing a cell subpopulation identified by CD151-low expression from the cardiomyocyte-containing cell population or by collecting a cell subpopulation identified by CD151-high expression from the cardiomyocyte-containing cell population.

2. The method according to claim 1, wherein the stem cells are induced pluripotent stem cells.

3. The method of claim 1, wherein CD151-high expression cell subpopulations and CD151-low expression subpopulations are separated by flow cytometry.

4. The method of claim 3, wherein the enriched atrial myocyte subpopulation or enriched ventricular myocyte subpopulation contains at least 10% more atrial or ventricular myocytes than the starting cardiomyocyte-containing cell population induced from stem cells.

* * * * *